(12) United States Patent
Bonjouklian et al.

(10) Patent No.: US 6,686,376 B2
(45) Date of Patent: Feb. 3, 2004

(54) METHODS AND COMPOUNDS FOR INHIBITING MRP1

(75) Inventors: Rosanne Bonjouklian, Zionsville, IN (US); Jeremy Schulenburg York, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/297,275

(22) PCT Filed: Jun. 12, 2001

(86) PCT No.: PCT/US01/10849

§ 371 (c)(1),
(2), (4) Date: Dec. 4, 2002

(87) PCT Pub. No.: WO02/00624

PCT Pub. Date: Jan. 3, 2002

(65) Prior Publication Data

US 2003/0232854 A1 Dec. 18, 2003

Related U.S. Application Data

(60) Provisional application No. 60/213,380, filed on Jun. 23, 2000.

(51) Int. Cl.[7] ........................ A61K 31/47; C07D 215/22
(52) U.S. Cl. ........................ 514/312; 546/155; 546/153; 546/152; 435/184
(58) Field of Search ................. 514/312, 311; 546/155, 153, 152; 435/184

(56) References Cited

FOREIGN PATENT DOCUMENTS

| WO | WO 99 51227 A | 10/1999 | |
|---|---|---|---|
| WO | WO 01 46199 A | 6/2001 | |
| WO | 01/46199 * | 6/2001 | ................. 514/293 |

* cited by examiner

*Primary Examiner*—Charanjit S. Aulakh
(74) *Attorney, Agent, or Firm*—Tina M. Tucker; Kirby W. Lee

(57) ABSTRACT

The present invention further relates to a method of inhibiting MRP1 in a mammal which comprises administering to a mammal in need thereof an effective amount of a compound of formula (I).

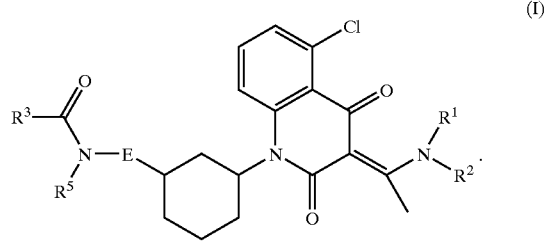

4 Claims, No Drawings

METHODS AND COMPOUNDS FOR INHIBITING MRP1

This application is a 371 of PCT/US01/10849 filed Jun. 12, 2000, now Ser. No. 02/00624. This application claims the benefit of Ser. No. 60/213,380 filed Jun. 23, 2000.

Along with surgery and radiotherapy, chemotherapy continues to be an effective therapy for many cancers. In fact, several types of cancer, such as Hodgkin's disease, large cell lymphoma, acute lymphocytic leukemia, testicular cancer and early stage breast cancer, are now considered to be curable by chemotherapy. Other cancers, such as ovarian cancer, small cell lung and advanced breast cancer, while not yet curable, are exhibiting positive response to combination chemotherapy.

One of the most important unsolved problems in cancer treatment is drug resistance. After selection for resistance to a single cytotoxic drug, cells may become cross-resistant to a whole range of drugs with different structures and cellular targets, e.g., alkylating agents, antimetabolites, hormones, platinum-containing drugs, and natural products. This phenomenon is known as multidrug resistance (MDR). In some types of cells this resistance is inherent, while in others, such as small cell lung cancer, it is usually acquired. Such resistance is known to be multifactorial and is conferred by at least two proteins: the 170 kDa P-glycoprotein (MDR1) and the more recently identified 190 kDa multidrug resistance protein (MRP1). Although both MDR1 and MRP1 belong to the ATP-binding cassette superfamily of transport proteins, they are structurally very different molecules and share less than 15% amino acid homology.

Despite the structural divergence between the two proteins, by 1994 there were no known consistent differences in the resistance patterns of MDR1 and MRP1 cell lines. However, the association, or lack thereof, of MRP1 and resistance to particular oncolytics is known. See Cole, et. al., "Pharmacological Characterization of Multidrug Resistant MRP-transfected Human Tumor Cells", *Cancer Research*, 54:5902–5910, 1994. Doxorubicin, daunorubicin, epirubicin, vincristine, and etoposide are substrates of MRP1, i.e., MRP1 can bind to these oncolytics and redistribute them away from their site of action, the nucleus, and out of the cell. Id. and Marquardt, D., and Center, M.S., *Cancer Research*, 52:3157, 1992.

Doxorubicin, daunorubicin, and epirubicin are members of the anthracycline class of oncolytics. They are isolates of various strains of Streptomyces and act by inhibiting nucleic acid synthesis. These agents are useful in treating neoplasms of the bone, ovaries, bladder, thyroid, and especially the breast. They are also useful in the treatment of acute lymphoblastic and myeloblastic leukemia, Wilm's tumor, neuroblastoma, soft tissue sarcoma, Hodgkin's and non-Hodgkin's lymphomas, and bronchogenic carcinoma.

Vincristine, a member of the vinca alkaloid class of oncolytics, is an isolate of a common flowering herb, the periwinkle plant (*Vinca rosea* Linn). The mechanism of action of vincristine is still under investigation but has been related to the inhibition of microtubule formation in the mitotic spindle. Vincristine is useful in the treatment of acute leukemia, Hodgkin's disease, non-Hodgkin's malignant lymphomas, rhabdomyosarcoma, neuroblastoma, and Wilm's tumor.

Etoposide, a member of the epipodophyllotoxin class of oncolytics, is a semisynthetic derivative of podophyllotoxin. Etoposide acts as a topoisomerase inhibitor and is useful in the therapy of neoplasms of the testis, and lung.

Additionally, PCT publications WO 99/51236, WO 99/51228, and WO 99/51227 disclose certain compounds known to be inhibitors of MRP1.

It is presently unknown what determines whether a cell line will acquire resistance via a MDR1 or MRP1 mechanism. Due to the tissue specificity of these transporters and/or in the case where one mechanism predominates or is exclusive, it would be useful to have a selective inhibitor of that one over the other. Furthermore, when administering a drug or drugs that are substrates of either protein, it would be particularly advantageous to coadminister an agent that is a selective inhibitor of that protein. It is, therefore, desirable to provide compounds that are selective inhibitors of MDR1 or MRP1.

The present invention relates to a compound of formula I:

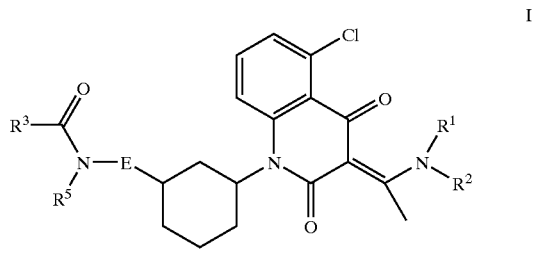

where:

E is a bond or —C(R$^4$)(R$^4$)—;

R$^1$ is independently at each occurrence hydrogen or C$_1$–C$_6$ alkyl;

R$^2$ is independently at each occurrence hydrogen or C$_1$–C$_6$ alkyl;

R$^3$ is independenty at each occurrence hydrogen, C$_1$–C$_6$ alkyl, optionally substituted C$_3$–C$_8$ cycloalkyl, optionally substituted (C$_1$–C$_4$ alkyl) C$_3$–C$_8$ cycloalkyl, optionally substituted (C$_1$–C$_4$ alkyl)-aryl, optionally substituted aryl, optionally substituted (C$_1$–C$_4$ alkyl)-heterocycle, optionally substituted heterocycle, C$_1$–C$_6$ alkoxy, optionally substituted O—(C$_3$–C$_8$ cycloalkyl), optionally substituted (C$_1$–C$_4$ alkoxy) C$_3$–C$_8$ cycloalkyl, optionally substituted (C$_1$–C$_4$ alkoxy)-aryl, optionally substituted O-aryl, optionally substituted (C$_1$–C$_4$ alkoxy)-heterocycle, or optionally substituted O-heterocycle;

R$^4$ is independently at each occurrence hydrogen or C$_1$–C$_6$ alkyl;

R$^5$ is independently at each occurrence hydrogen or C$_1$–C$_6$ alkyl;

or a pharmaceutical salt thereof.

The present invention further relates to a method of inhibiting MRP1 in a mammal which comprises administering to a mammal in need thereof an effective amount of a compound of formula I.

In another embodiment, the present invention relates to a method of inhibiting a resistant neoplasm, or a neoplasm susceptible to resistance in a mammal which comprises administering to a mammal in need thereof an effective amount of a compound of formula I in combination with an effective amount of an oncolytic agent.

The present invention also relates to a pharmaceutical formulation comprising a compound of formula I in combination with one or more oncolytics, pharmaceutical carriers, diluents, or excipients therefor.

Additionally, the present invention relates to a pharmaceutical formulation comprising a compound of formula I.

The current invention concerns the discovery that compounds of formula I are selective inhibitors of multidrug resistant protein (MRP1), and are thus useful in treating MRP1 conferred multidrug resistance (MDR) in a resistant neoplasm and a neoplasm susceptible to resistance.

The terms "inhibit" as it relates to MRP1 and "inhibiting MRP1" refer to prohibiting, alleviating, ameliorating, halting, restraining, slowing or reversing the progression of, or reducing MRP1's ability to redistribute an oncolytic away from the oncolytic's site of action, most often the neoplasm's nucleus, and out of the cell.

As used herein, the term "effective amount of a compound of formula I" refers to an amount of a compound of the present invention which is capable of inhibiting MRP1. The term "effective amount of an oncolytic agent" refers to an amount of oncolytic agent capable of inhibiting a neoplasm, resistant or otherwise.

The term "inhibiting a resistant neoplasm, or a neoplasm susceptible to resistance" refers to prohibiting, halting, restraining, slowing or reversing the progression of, reducing the growth of, or killing resistant neoplasms and/or neoplasms susceptible to resistance.

The term "resistant neoplasm" refers to a neoplasm, which is resistant to chemotherapy where that resistance is conferred in part, or in total, by MRP1. Such neoplasms include, but are not limited to, neoplasms of the bladder, bone, breast, lung(small-cell), testis, and thyroid and also includes more particular types of cancer such as, but not limited to, acute lymphoblastic and myeloblastic leukemia, Wilm's tumor, neuroblastoma, soft tissue sarcoma, Hodgkin's and non-Hodgkin's lymphomas, and bronchogenic carcinoma.

A neoplasm, which is "susceptible to resistance", is a neoplasm where resistance is not inherent nor currently present but can be conferred by MRP1 after chemotherapy begins. Thus, the methods of this invention encompass a prophylactic and therapeutic administration of a compound of formula I.

The term "chemotherapy" refers to the use of one or more oncolytic agents where at least one oncolytic agent is a substrate of MRP1. A "substrate of MRP1" is an oncolytic that binds to MRP1 and is redistributed away from the oncolytics site of action (the nucleus of the neoplasm) and out of the cell, thus, rendering the therapy less effective. Preferred oncolytic agents are doxorubicin, daunorubicin, epirubicin, vincristine, and etoposide.

The terms "treat" or "treating" bear their usual meaning which includes preventing, prohibiting, alleviating, ameliorating, halting, restraining, slowing or reversing the progression, or reducing the severity of MRP1 derived drug resistance in a multidrug resistant tumor.

In the general formulae of the present document, the general chemical terms have their usual meanings. For example, the term "$C_1$–$C_4$ alkyl" refers to methyl, ethyl, propyl, isopropyl, cyclopropyl, butyl, cyclobutyl, s-butyl, and t-butyl. The term "$C_1$–$C_6$ alkyl" refers to a monovalent, straight or branched saturated hydrocarbon containing from 1 to 6 carbon atoms. Additionally, the term "$C_1$–$C_6$ alkyl" includes $C_1$–$C_4$ alkyl groups and $C_3$–$C_6$ cycloalkyls. The term "$C_1$–$C_6$ alkyl" includes, but is not limited to, cyclopentyl, pentyl, hexyl, cyclohexyl, and the like. The term "$C_3$–$C_8$ cycloalkyl" refers to cyclopropyl, cyclobutyl, cyclopentyl, cyclohexyl, cycloheptyl, and cyclooctyl. The term "$C_5$–$C_7$ cycloalkyl" refers to cyclopentyl, cyclohexyl, and cycloheptyl. The term "$C_6$–$C_{10}$ bicycloalkyl" refers to bicyclo-[2.1.1]hexanyl, [2.2.1]heptanyl, [3.2.1]octanyl, [2.2.2]octanyl, [3.2.2]nonanyl, [3.3.1]nonanyl, [3.3.2]decanyl, and [4.3.1]decanyl ring systems.

The terms "$C_1$–$C_4$ alkoxy" and "$C_1$–$C_6$ alkoxy" refer to moieties of the formula O—($C_1$–$C_4$ alkyl) and O—($C_1$–$C_6$ alkyl) respectively.

The term "optionally substituted $C_3$–$C_8$ cycloalkyl" refers to a $C_3$–$C_8$ cycloalkyl unsubstituted or substituted once with a phenyl, substituted phenyl, or $CO_2R^1$ group.

The terms "optionally substituted ($C_1$–$C_4$ alkyl)-($C_3$–$C_8$ cycloalkyl)" refers to optionally substituted $C_3$–$C_8$ cycloalkyl linked through a $C_1$–$C_4$ alkyl, optionally substituted with halo or hydroxy.

The term "optionally substituted $C_6$–$C_{10}$ bicycloalkyl" refers to a $C_6$–$C_{10}$ bicycloalkyl unsubstituted or substituted once with a phenyl, substituted phenyl, or $CO_2R^1$ group.

The term "halo" or "halide" refers to fluoro, chloro, bromo, and iodo.

The term "aryl" refers to phenyl and naphthyl.

The terms "optionally substituted aryl" refers to a phenyl and naphthyl group respectively optionally substituted from 1 to 5 times independently with $C_1$–$C_6$ alkyl, $C_1$–$C_4$ alkoxy, halo, hydroxy, trifluoromethyl, $NR^4R^5$, $SO_2NR^4R^5$, MH—Pg, $C_1$–$C_6$ alkoxy, benzyloxy, $C(O)R^4$, $C_5$–$C_7$ cycloalkyl, trifluoromethoxy, $SR^1$, cyano, or nitro.

The terms "optionally substituted ($C_1$–$C_4$ alkyl)aryl" refers to optionally substituted aryl linked through a $C_1$–$C_4$ alkyl, optionally substituted with halo, trifluoromethyl, or hydroxy.

The term "heterocycle" is taken to mean stable unsaturated and saturated 3 to 6 membered rings containing from 1 to 4 heteroatoms selected from the group consisting of nitrogen, oxygen and sulfur, said rings being optionally benzofused. All of these rings may be substituted with up to three substituents independently selected from the group consisting of halo, $C_1$–$C_4$ alkoxy, $C_1$–$C_4$ alkyl, cyano, nitro, hydroxy, —S(O)$_m$—($C_1$–$C_4$ alkyl) and —S(O)$_m$-phenyl where m is 0, 1 or 2. Saturated rings include, for example, pyrrolidinyl, piperidinyl, piperazinyl, tetrahydrofuryl, oxazolidinyl, morpholino, dioxanyl, pyranyl, and the like. Benzofused saturated rings include indolinyl, 1,2,3,4-tetrahydroquinolinyl, 1,2,3,4-tetrahydroisoquinolinyl and the like. Unsaturated rings include furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like. Benzofused unsaturated rings include isoquinolinyl, benzoxazolyl, benzthiazolyl, quinolinyl, benzofuranyl, thionaphthyl, indolyl and the like.

The term "substituted heterocycle" refers to a heterocyclic ring substituted 1 or 3 times independently with a $C_1$–$C_6$ alkyl, halo, benzyl, phenyl, trifluoromethyl. Saturated heterocyclic rings may be additionally substituted 1 or 2 times with an oxo group, however, total substitution of the saturated heterocyclic ring may not exceed two substituents.

The terms "optionally substituted ($C_1$–$C_4$ alkyl)-heterocycle" refers to optionally substituted heterocycle linked through a $C_1$–$C_4$ alkyl, optionally substituted with halo or hydroxy.

The term "amino acid ester" as used in this specification refers to an amino acid where the carboxy group is substituted with a $C_1$–$C_6$ alkyl or benzyl group. That is, the alkyl group when taken together with the carboxy group forms a $C_1$–$C_6$ alkyl ester. A skilled artisan would appreciate that some amino acids have two carboxy groups that may be substituted with a $C_1$–$C_6$ alkyl group, for example, aspartic acid and glutamic acid. This invention contemplates the possibility of amino acid mono- or diesters in these circumstances.

The term "protecting group" (Pg) refers to an amino protecting group or a hydroxy protecting group. The species of protecting group will be evident from whether the "Pg" group is attached to a nitrogen atom (amino protecting group) or attached to an oxygen atom (hydroxy protecting group).

The term "amino protecting group" as used in this specification refers to a substituent(s) of the amino group commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("PMOC"), and the like; and like amino protecting groups. The species of amino protecting group employed is not critical so long as the derivatized amino group is stable to the condition of subsequent reaction (s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by T. W. Greene, "Protective Groups in Organic Synthesis", John Wiley and Sons, New York, N.Y., 1991, Chapter 7 hereafter referred to as "Greene". A preferred amino protecting group is t-butyloxycarbonyl.

The term "hydroxy protecting group" denotes a group understood by one skilled in the organic chemical arts of the type described in Chapter 2 of Greene. Representative hydroxy protecting groups include, for example, ether groups including methyl and substituted methyl ether groups such as methyl ether, methoxymethyl ether, methylthiomethyl ether, tert-buylthiomethyl ether, (phenyldimethylsilyl) methoxy-methyl ether, benzyloxymethyl ether, p-methoxybenzyloxy-methyl ether, and tert-butoxymethyl ether; substituted ethyl ether groups such as ethoxyethyl ether, 1-(2-chloroethoxy)ethyl ether, 2,2,2-trichloroethoxymethyl ether, and 2-(trimethylsilyl)ethyl ether; isopropyl ether groups; phenyl and substituted phenyl ether groups such as phenyl ether, p-chlorophenyl ether, p-methoxyphenyl ether, and 2,4-dinitrophenyl ether, benzyl and substituted benzyl ether groups such as benzyl ether, p-methoxybenzyl ether, o-nitrobenzyl ether, and 2,6-dichlorobenzyl ether, and alkylsilyl ether groups such as trimethyl- triethyl- and triisopropylsilyl ethers, mixed alkylsilyl ether groups such as dimethylisopropylsilyl ether, and diethylisopropylsilyl ether; and ester protecting groups such as formate ester, benzylformate ester, mono-, di-, and trichloroacetate esters, phenoxyacetate ester, and p-chlorophenoxyacetate and the like. The species of hydroxy protecting group employed is not critical so long as the derivatized hydroxy group is stable to the conditions of subsequent reaction(s) on other positions of the intermediate molecule and can be selectively removed at the appropriate point without disrupting the remainder of the molecule including any other hydroxy protecting group(s).

The term "carbonyl activating group" refers to a substituent of a carbonyl that increases the susceptibility of that carbonyl to nucleophilic addition. Such groups include, but are not limited to, alkoxy, aryloxy, nitrogen containing unsaturated heterocycles, or amino groups such as oxybenzotriazole, imidazolyl, nitrophenoxy, pentachlorophenoxy, N-oxysuccinimide, N,N'-dicyclohexylisoure-O-yl, N-hydroxy-N-methoxyamino, and the like; acetates, formates, sulfonates such as methanesulfonate, ethanesulfonate, benzenesulfonate, or p-toluenylsulfonate, and the like; and halides especially chloride, bromide, or iodide.

The term "carbonyl activating reagent" refers to a reagent that converts the carbonyl of a carboxylic acid group to one that is more prone to nucleophilic addition and includes, but is not limited to, such reagents as those found in "The Peptides", Gross and Meienhofer, Eds., Academic Press (1979), Ch. 2 and M. Bodanszky, "Principles of Peptide Synthesis", 2$^{nd}$ Ed., Springer-Verlag Berlin Heidelberg, 1993, hereafter referred to as "The Peptides" and "Peptide Synthesis" respectively. Specifically, carbonyl activating reagents include thionyl bromide, thionyl chloride, oxalyl chloride, and the like; alcohols such as nitrophenol, pentachlorophenol, and the like; amines such as N-hydroxy-N-methoxyamine and the like; acid halides such as acetic, formic, methanesulfonic, ethanesulfonic, benzenesulfonic, or p-tolylsulfonic acid halide, and the like; and compounds such as 1,1'-carbonyldiimidazole, benzotriazole, imidazole, N-hydroxysuccinimide, dicyclohexylcarbodiimide, and the like.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical Salts", *J. Pharm. Sci.*, 66:1, 1977. Typical pharmaceutical salts include those salts prepared by reaction of the compounds of formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The term "base addition salt" refers to a salt of a compound of formula I prepared by reaction of a compound of formula I with a mineral or organic base. For exemplification of pharmaceutical base addition salts see, e.g., Berge, S. M, Bighley, L. D., and Monkhouse, D. C., *J. Pharm. Sci.*, 66:1, 1977. This invention also contemplates pharmaceutical base addition salts of compounds of formula I. The skilled artisan would appreciate that some compounds of formula I may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of formula I.

While all of the compounds of the present invention are useful, certain of the compounds are particularly interesting and are preferred. The following listing sets out several groups of preferred compounds. It will be understood that each of the listings may be combined with other listings to create additional groups of preferred embodiments.

1) E is a bond;
2) E is $-C(R^4)(R^4)-$;
3) When E is $-C(R^4)(R^4)$, $R^4$ is hydrogen;
4) When E is $-C(R^4)(R^4)$, $R^4$ is methyl;
5) $R^1$ and $R^2$ are hydrogen;
6) $R^3$ is $C_1-C_6$ alkyl;
7) $R^3$ is optionally substituted $C_3-C_8$ cycloalkyl;
8) $R^3$ is optionally substituted ($C_1-C_4$ alkyl) $C_3-C_8$ cycloalkyl;
9) $R^3$ is optionally substituted ($C_1-C_4$ alkyl)-aryl;
10) $R^3$ is optionally substituted aryl;
11) $R^3$ is optionally substituted ($C_1-C_4$ alkyl)-heterocycle;
12) $R^3$ is optionally substituted heterocycle, $C_1-C_6$ alkoxy,
13) $R^3$ is optionally substituted O—($C_3-C_8$ cycloalkyl);
14) $R^3$ is optionally substituted ($C_1-C_4$ alkoxy) $C_3-C_8$ cycloalkyl;
15) $R^3$ is optionally substituted ($C_1-C_4$ alkoxy)-aryl;
16) $R^3$ is optionally substituted O-aryl;
17) $R^3$ is optionally substituted ($C_1-C_4$ alkoxy)-heterocycle;
18) $R^3$ is optionally substituted O-heterocycle;
19) $R^5$ is hydrogen;
20) $R^5$ is methyl;
21) The compound is a pharmaceutical salt; and
22) The compound is the hydrochloride salt.

The compounds of the present invention can be prepared by a variety of procedures, some of which are illustrated in the Schemes below. The particular order of steps required to produce the compounds of formula I is dependent upon the particular compound being synthesized, the starting compound, and the relative lability of the substituted moieties.

Compounds of formula I may be prepared from compounds of formula II as illustrated in Scheme 1 below, wherein Y is $C(O)R^4$ or $-E-NR^5C(O)R^3$, $R^1$ and $R^2$ are hydrogen, and E, $R^3$, $R^4$, and $R^5$ are as described supra.

Scheme 1

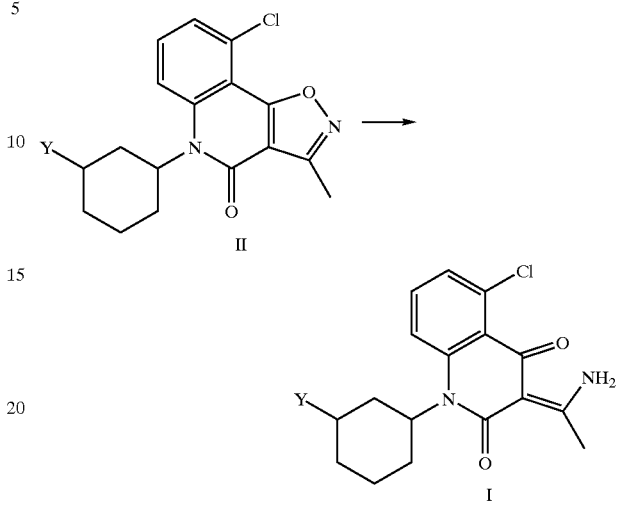

Compounds of formula I may be prepared by combining a compound of formula II in a suitable solvent, preferably acetonitrile/water (5:1 ratio), and adding a suitable reducing agent, such as hexacarbonylmolybdenum.

The reactants are typically combined at a temperature from about 0° C. to about 100° C. The reactants are preferably combined at room temperature and the resulting solution is typically heated to reflux and mixed until the reaction is complete, as measured by the consumption of the substrate. The final product may be isolated and/or purified by standard techniques well known in the art.

Compounds of formula II may be prepared from compounds of formula III as illustrated in Scheme 2 below, wherein Y is $C(O)R^4$ or $-E-NR^5C(O)R^3$.

Scheme 2

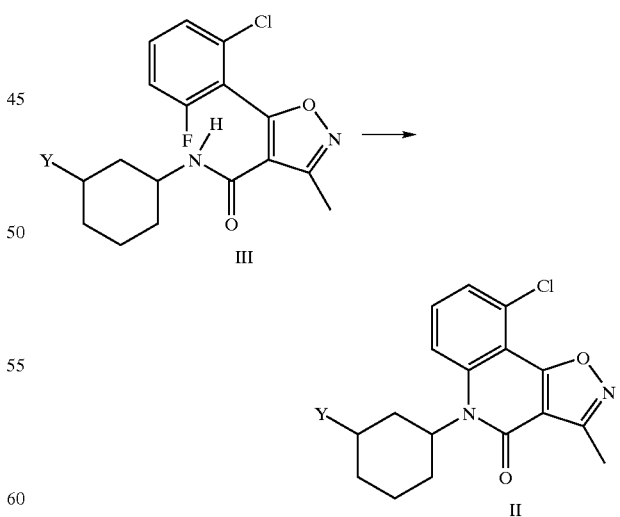

Compounds of formula II may be prepared by dissolving or suspending a compound of formula III in a suitable solvent, preferably dimethylformamide, and adding a suitable base, such as potassium methoxide, potassium tert-butoxide, potassium carbonate, sodium hexamethyldisilazane, or preferably potassium hexamethyldisilazane. The base is typically employed in an one to one ratio. However, as the skilled artisan would appreciate, a slight molar excess, usually in about a 1.1 to about a 3 fold molar excess relative to the compound of formula III, is acceptable.

The reactants are typically combined at a temperature from about 0° C. to about 100° C. The reactants are preferably combined at room temperature and the resulting solution is typically mixed for from about 5 minutes to about 18 hours, preferably from about 15 minutes to about 3 hours.

Any protecting groups remaining in the cyclized compound of formula I may be removed as taught in Greene to provide the compounds of formula II. Preferred choices of protecting groups and methods for their removal may be found in the Preparations and Examples sections below.

Compounds of formula II may be prepared from compounds of formula (i) as illustrated in Scheme 3 below where E, $R^3$, $R^4$, and $R^5$ are as described supra.

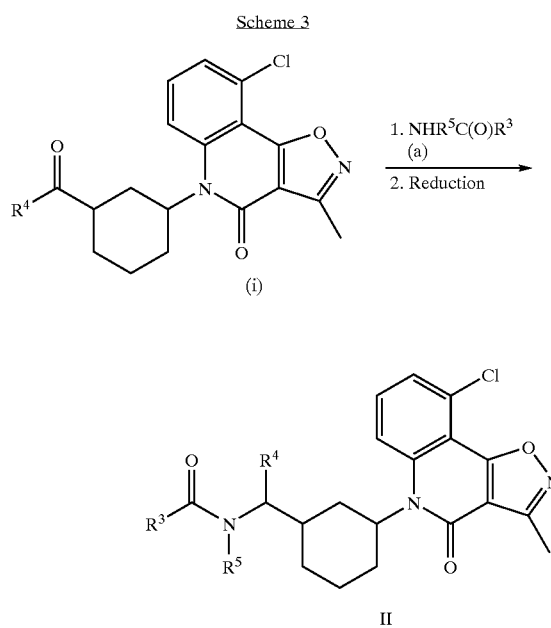

The compounds of formula (i) may be reductively aminated to form the compounds of formula II. Reductive aminations are well known transformations, see, e.g., Larock, "Comprehensive Organic Transformations", pg. 421, VCH Publishers, New York, N.Y., 1989, hereafter referred to as "Larock".

Amines of formula (a) may be dissolved or suspended in a suitable solvent, optionally in the presence of a suitable base, preferably N-methyl morpholine or triethylamine, when the compound of formula III is an acid addition salt to convert the salt to its free amine form, and a compound of formula (i) is added. A Lewis acid catalyst, such as titanium (IV) isopropoxide, may optionally be employed. Once it is determined that the compound of formula (i) has been substantially consumed, the intermediate is typically reacted in situ with a suitable reducing agent to provide the compounds of formula II. The overall conversion may be performed at about 0° C. to the boiling point of the mixture, but room temperature is a preferred reaction temperature. The formation of the compounds of formula II may take from 15 minutes to 24 hours as measure by the consumption of the compound of formula (i). Methanol is typically a preferred solvent.

Suitable reducing agents include, but are not limited to, hydrogen over palladium or platinum on carbon, borane or complexes of borane, e.g., borane-pyridine, borane-t-butylamine, and borane-dimethylamine complex; and borohydride reducing agents such as sodium borohydride or sodium cyanoborohydride. Sodium cyanoborohydride is a preferred reducing agent.

Compounds of formula (ii) and (iii) may be combined to prepared compounds of formula III according to Scheme 4, wherein Y is defined supra.

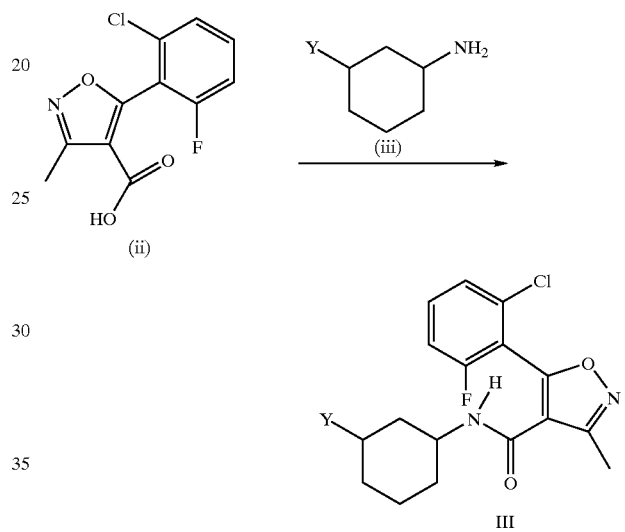

Compounds of formula (ii) may be converted to the corresponding acid halide by methods well known to one skilled in the art. Compounds of formula III may be prepared by dissolving or suspending an acid halide of a compound of formula (ii) in a suitable solvent and adding a compound of formula (iii) in a suitable solvent. Triethylamine or dimethylformamide is a suitable solvent and is typically preferred for the compound of formula (ii). A 1:1 mixture of DMF and dichloromethane is a convenient solvent and is typically preferred for the amine of formula (iii). This amide forming reaction is also preferably run in the presence of 4-dimethylaminopyridine (DMAP).

The compound of formula (ii) is preferably employed in an equimolar amount, relative to the compound of formula (iii), but a slight excess (about a 0.05 to about 0.15 molar excess) is acceptable. DMAP is employed in a catalytic fashion. For example, about 5 molar percent to about 15 molar percent, relative to the compound of formula (iii), is typically employed. A 10 molar percent is usually preferred.

Compounds of formula (iii), wherein Y is defined supra, are well known in the art and to the extent not commercially available, are readily synthesized by standard procedures commonly employed in the art.

The synthesis of compounds of formula (ii) may be performed as described in Route 1 below.

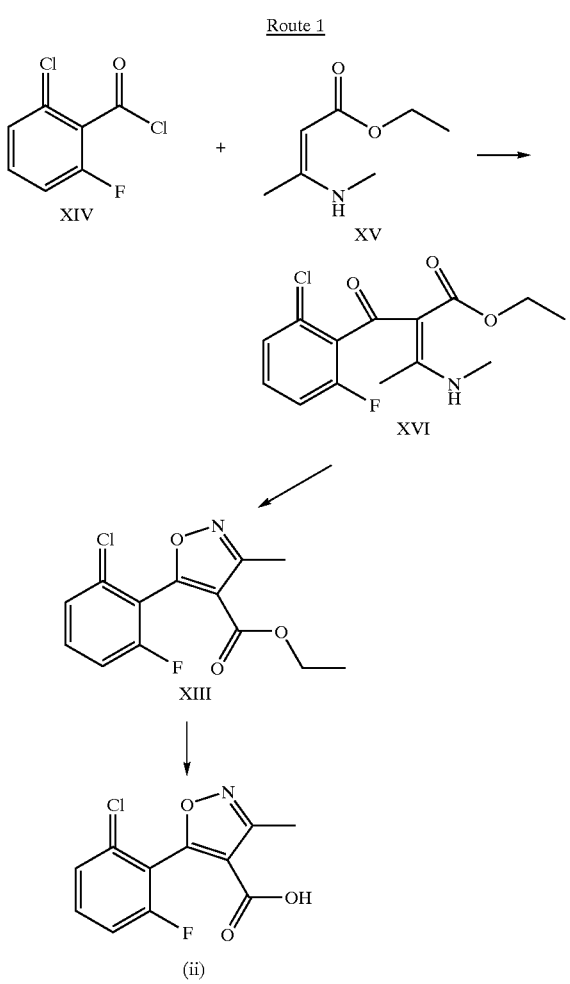

Compounds of formula XVI may be prepared by dissolving or suspending a compound of formula XV and a suitable base in a suitable solvent and adding a compound of formula XIV in a suitable solvent, dropwise. Toluene is a convenient solvent and is typically preferred. Triethylamine is the preferred base. The compound of formula XIV is typically and preferably employed in an equimolar amount, relative to the compound of formula XV, but a slight excess is acceptable.

The reactants are preferably combined at about 0° C. and the resulting solution is typically warmed to room temperature and mixed for from about 18 hours to about 24 hours.

The compound of formula XVI may then be converted to the compound of formula XIII by dissolving or suspending a compound of formula XVI in a suitable acidic solvent and adding hydroxylamine hydrochloride. Glacial acetic acid is a convenient acidic solvent and is typically preferred. The ester group is then hydrolyzed to the corresponding carboxylic acid of formula (ii) through standard procedures commonly employed in the art, see for example, *Larock*, pgs 981–985.

The reactants are preferably combined at about room temperature then heated to reflux for from about 30 minutes to about 60 minutes. Preferably the reaction is heated to reflux from about 40 to 45 minutes.

Compounds of formula XIV and XV are known in the art and, to the extent not commercially available, are readily synthesized by standard procedures commonly employed in the art.

Compounds of formula XIX may be prepared in a manner similar to that described in the literature, for example, see Liu K, Shelton B R, Howe, R K, *J. Org. Chem.*, 1980, 45, 3916–3918.

The pharmaceutical salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The optimal time for performing the reactions of the Schemes and the Route can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of formula I may be further purified, if desired by common techniques such as recrystallization or chromatography over solid supports such as silica gel or alumina The skilled artisan will appreciate that not all substituents are compatible with all reaction conditions. These compounds may be protected or modified at a convenient point in the synthesis by methods well known in the art.

The following Preparations and Examples are provided to better elucidate the practice of the present invention and should not be interpreted in any way as to limit the scope of same. Those skilled in the art will recognize that various modifications may be made while not departing from the spirit and scope of the invention. All publications mentioned in the specification are indicative of the level of those skilled in the art to which this invention pertains. The terms and abbreviations used in the instant Preparations and Examples have their normal meanings unless otherwise designated. For example "° C.", "N", "mmol", "g", "mL", "M", "HPLC", "IR", "MS(FD)", "MS(IS)", "MS(FIA)", "MS (FAB)", "MS(EI)", "MS(ES)", "UV", and "$^1$H NMR", refer to degrees Celsius, normal or normality, millimole or millimoles, gram or grams, milliliter or milliliters, molar or molarity, high performance liquid chromatography, infra red spectrometry, field desorption mass spectrometry, ion spray mass spectrometry, flow injection analysis mass spectrometry, fast atom bombardment mass spectrometry, electron impact mass spectrometry, electron spray mass spectrometry, ultraviolet spectrometry, and proton nuclear magnetic resonance spectrometry respectively. In addition, the absorption maxima listed for the IR spectra are only those of interest and not all of the maxima observed.

PREPARATION 1

3-Methyl-5-(2-chloro-6-fluorophenyl)-4-isoxazolecarboxylic Acid Ethyl Ester

To a solution of ethyl 3-aminomethyl crotonate (4.79 g, 33.5 mmol) in toluene (10 mL), was added triethylamine (3.73 g, 37 mmol). The solution was chilled using an ice bath, and then 2-chloro-6-fluorobenzoyl chloride (6.47 g, 33.5 mmol) was added dropwise over a 20 min period. The reaction was allowed to warm slowly to r.t., and stirred for 24 hr. The resulting suspension was then filtered, and the filtrate diluted with ethyl acetate (100 mL) and transferred to a separatory funnel. The organic layer was sequentially washed with water, brine, dried (sodium sulfate), and the volatiles removed under reduced pressure to provide 2-(2-chloro-6-fluorobenzoyl)-3-methylamino-but-2-enoic acid ethyl ester (9.46 g) as a golden solid, and primarily one geometrical isomer.

NMR (CDCl$_3$) δ 6.95–7.4 (3 m, 3 H), 3.8 (m, 2H, OEt), 3.12 (d, 3H, —NCH$_3$), 2,4 (s, 3H, vinyl CH$_3$), 0.8 (t, OEt). MS (ES) m/z 299.9 (M+H)$^+$.

Crude adduct was then redissolved in glacial HOAc (50 mL) to which was added NH$_2$OH.HCl (1.8 g, 1.1 eq). The solution was then heated to reflux for 40–45 min to effect isoxazole formation. The reaction mixture was concentrated to an oil, diluted with ether, and transferred to a sep. funnel. The organic phase was washed with saturated bicarbonate, brine, then dried. Filtration and concentration afforded crude isoxazole ethyl ester (7.5 g), which could be used without further purification.

MS (+ES) m/z 283.9 (M+H)$^+$.

PREPARATION 2

4-Isoxazolecarboxylic Acid, 3-Methyl, 5-(2-Chloro-6-fluorophenyl)

Hydrolysis of the ethyl ester was accomplished by dissolving the crude ester (7.5 g, approx. 0.027 mol) in TBF (250 mL), and adding aq. LiOH (1.344 g in 100 mL, 2 eq).

After stirring overnight at r.t., the solution was concentrated to $\frac{2}{3}^{rd}$ volume, diluted with EtOAc (200 mL) and 50 mL water, transferred to a separatory funnel, and the aqueous phase collected. The organic phase was washed twice, and the combined aqueous phase was then acidified with 5N HCl. Back extraction with three washings of EtOAc was then followed with a brine wash of the combined organics. After drying over Na$_2$SO$_4$, filtration and concentration, clean isoxazole acid was obtained (2.94 g).

MS (−ES) m/z 253.8, 255.8 (M−H)$^−$.

PREPARATION 3

2-{3-[(T-butoxy)carbonylamino]cyclohexyl}acetic Acid

Phenylmethyl-2-{(3S,1R)-3-[(t-butoxy)carbonylamino]-cyclohexyl}acetate (1.0 g; 2.77 mmol) was dissolved in tetrahydrofuran (4 mL) and ethanol (4 mL) under a dry nitrogen atmosphere at room temperature. This cloudy white solution became clear and colorless after mixing with 2N NaOH$_{(aq)}$ (15 mL; 19.4 mmol; 11.1 equiv) for 2 h. After rotary evaporation to dryness, the white solid was dissolved in water (20 mL) and the resulting solution extracted with diethyl ether (twice). Acidification of the aqueous layer to pH 2 with 1N HCl$_{(aq)}$ produced a white solid that was extracted into ethyl acetate (thrice). The ethyl acetate was washed with saturated NaCl$_{(aq)}$, dried with Na$_2$SO$_{4(s)}$, and concentrated to dryness by rotary evaporation. The resulting white solid (700 mg; 98% yield) was used in subsequent reactions without further purification.

MS(ES) calc'd: [M+Na]$^+$=280.2 m/z, [M−H]$^−$=256.2 m/z. Found: 280.1 m/z; 256.2 m/z.

PREPARATION 4

N-((1S,3R)-3-{[(Phenylmethoxy)carbonylamino] methyl}cyclohexyl)(t-butoxy)carboxamide To a solution of 2-{3-[(t-butoxy)carbonylamino] cyclohexyl}acetic acid (3.43 g, 13.35 mmol), Et$_3$N (3.75 mL, 26.96 mmol) in toluene (86 mL) under N$_2$ was added DPPA (5.8 mL, 26.96 mmol) and benzyl alcohol (4.28 mL, 41.38 mmol). The solution was heated to reflux overnight. The reaction was cooled to room temperature, diluted with EtOAc, washed (1.0N NaOH then brine), dried (MgSO$_4$), filtered, and concentrated. Column chromatography (silica gel, hexanes/EtOAc gradient) gave the title compound (3.05 g, 63%). Mass Spectrum (ES+) (m/z) 263.1 [M−BOC].

PREPARATION 5

(cis-3(S)-Aminocyclohexylmethyl)carbamic Acid Benzyl Ester

S-amino enantiomer of a compound from preparation 4 (1.0 g, 2.76 mmol) was treated with TFA (5 mL) under N$_2$. After 20 min of stirring at r.t. the reaction was complete. The crude was then concentrated to an oil which was purified on a Varian Bond-Elut SCX column (10 g). The column was eluted consecutively with CHCl$_3$, MeOH, and ammonia (2.0M in MeOH). The pure product was recovered from the ammonia fractions. The solvent was removed in vacuo to afford 0.632 g (87%) as a colorless oil. MS (ES+) m/z 263.0 (M+H)$^+$.

PREPARATION 6

(1S,3R)(3-{[5-(2-Chloro-6-fluorophenyl)-3-methylisoxazole-4-carbonyl] amino}cyclohexylmethyl)carbamic Acid Benzyl Ester A solution from preparation 2 (1.0 g, 3.9 mmol) in toluene (30 mL) was treated with a catalytic amount of pyridine (0.1 mL) and cooled to 0° C. The solution was then treated with oxalyl chloride (0.545 g, 4.3 mmol) and stirred at r.t for 2 hr. 1H NMR showed the completion of the acid chloride formation; 7.52 (d, 1H), 7.37 (d, 1H), 7.15 (t, 1H). The solvent was removed in vacuo. A solution from preparation 5 (0.550 g, 2.09 mmol) and triethylamine (0.422 g, 4.18 mmol) in dry DMF (25 mL) was stirred at r.t. This solution was then treated with the acid chloride from above (0.859 g, 3.135 mmol) which was added dropwise over two min. The reaction was then catalyzed with DMAP (0.025 g, 0.21 mmol) and allowed to stir o.n. The reaction was diluted in EtOAc (250 mL), transferred to a sep funnel, and washed with a 5% citric acid solution (5×50 mL), sat. sodium bicarbonate solution (2×50 mL), brine (2×50 mL) and was dried over sodium sulfate. The EtOAc solution was filtered and the solvent removed in vacuo to yield an orange solid. The solid was purified using silica gel column chromatography. The column was prepared with $CHCl_3$ and the product was eluted with 10% EtOAc in $CHCl_3$. The solvent was removed in vacuo to afford 0.584 g (56%) of the title compound as a white solid. MS (ES+) m/z 500.1 $(M+H)^+$.

PREPARATION 7

(1R,3S)-[3-(9-Chloro-3-methyl-4-oxo-5H-isoxazolo [4,5-c]quinolin-5-yl)-cyclohexylmethyl]-carbamic Acid Benzyl Ester A solution of the product from preparation 6 (0.534 g, 1.1 mmol) in dry DWM (20 mL) was stirred and cooled to 0° C. in an ice bath. The reaction was then treated with KHMDS-0.5M in toluene (4.300 mL, 2.140 mmol) dropwise over 5 min and allowed to warm back to r.t. The reaction was complete in 25 min. The reaction mixture was then diluted in EtOAc (200 mL), transferred to a sep funnel, and washed consecutively with 5% citric acid solution (4×50 mL), sat sodium bicarbonate (2×50 mL), brine (2×50 mL), and dried over sodium sulfate. The solvent was removed in vacuo to afford a yellow-white solid. The solid was purified using silica gel column chromatography and an eluting solvent of 100% $CHCl_3$. The solvent was removed in vacuo to afford 0.401 g (78%) as a white solid. MS (ES+) m/z 480.1 $(M+H)^+$.

PREPARATION 8

(1R,3S)-5-(3-Aminomethyl-cyclohexyl)-9-chloro-3-methyl-5H-isoxazolo[4,5-c]quinolin-4-one A solution of the product from preparation 7 (0.40 g, 0.83 mmol) in dry $CH_2Cl_2$ (5 mL) was treated with iodotrimethylsilane (0.25 g, 1.25 mmol) and stirred at rt. After 3 hr the reaction was quenched with MeOH (2 mL) and stirred for an additional 30 min. The solution was then concentrated to an orange solid and taken up in EtOAc (20 mL) and 1 N HCl (20 mL) and transferred to a sep funnel. The organic layer was extracted and the aqueous layer was washed with additional EtOAc (2×10 mL). The pH of the aqueous layer was then adjusted to ph~12 with 5 M NaOH. The product was extracted with EtOAc (3×25 mL). The EtOAc extractions were dried over sodium sulfate, filtered, and the solvent removed in vacuo to afford 0.240 g (84%) as a white solid which was used without further purification. MS (ES+) m/z 346.0 $(M+H)^+$.

PREPARATION 9

(1R,3S)-N-[3-(9-Chloro-3-methyl-4-oxo-5H-isoxazolo[4,5-c]quinolin-5-yl)-cyclohexylmethyl]-nicotinamide A solution of the product from preparation 8 (0.342 g, 0.99 mmol) and nicotinoyl chloride (0.210 g, 1.49 mmol) in $CH_2Cl_2$ (25 mL) was treated with triethylamine (0.1 g, 0.99 mmol) and stirred o.n. at r.t. The reaction was concentrated to a solid and diluted in EtOAc (50 mL), washed with a sat. bicarbonate solution (3×25 mL), brine (2×25 mL), and dried over sodium sulfate. The solvent was removed in vacuo to afford a yellow oil. The oil was purified by silica gel column chromatography. The column was prepared using 100% EtOAc and the product was eluted off the column with 5% MeOH in EtOAc. The solvent was removed in vacuo to afford 0.185 g (41%) as a white solid. MS (ES+) m/z 451.0 $(M+H)^+$, (ES−) m/z 449.0 $(M-H)^-$, 509.1 $(M+CH_3COO^-)^-$.

PREPARATION 10

N-[3-(9-Chloro-3-methyl-4-oxo-5H-isoxazolo[4,5-c] quinolin-5-yl)-cyclohexylmethyl]-6-fluoro-nicotinamide 6-Fluoro-nicotinic acid (0.05 g, 0.35 mmol) and oxalyl chloride (0.055 g, 0.44 mmol) were combined in toluene (10 mL) and stirred for 2 hr at 80 ° C. to form the acid chloride. The reaction was concentrated to a solid and added directly to a solution of a compound from preparation 9 (0.1 g, 0.29 mmol) in $CH_2Cl_2$ (15 mL). The reaction was treated with excess $Et_3N$ (0.06 g, 0.58 mmol) and stirred at room temperature overnight. The reaction was then diluted in $CH_2Cl_2$ (85 mL) and washed with a saturated sodium bicarbonate solution (3×50 mL) and brine (2×50 mL). The organic solution was dried over sodium sulfate, filtered, and the solvent removed to afford a crude yellow solid The solid was purified on a chromatotron using a 1 cm thick silica gel plate. The product was eluted with 50% EtOAc in $CH_2Cl_2$. The solvent was removed to afford 0.084 g (61%) of the title compound as a white solid. MS m/z (ES+) 468.8 $(M+H)^+$, (ES−) 466.8 $(M-H)^-$, 526.8 $(M+CH3COO^-)^-$.

PREPARATION 11

(1R,3S)-N-[3-(9-Chloro-3-methyl-4-oxo-5H-isoxazolo[4,5-c]quinolin-5-yl)-cyclohexylmethyl]-benzamide A solution of the product from preparation 8 (0.240 g, 0.696 mmol) and benzoyl chloride (0.147 g, 1.044 mmol) in $CH_2Cl_2$ (5 mL) was treated with triethylamine (0.07 g, 0.696 mmol) and stirred o.n. at r.t. The reaction was diluted in $CH_2Cl_2$ (25 mL), washed with a 5% citric acid solution (2×10 mL), brine (2×10 mL), and dried over sodium sulfate. The solvent was removed in vacuo to afford a yellow oil. The oil was purified by silica gel column chromatography. The column was prepared using 2:1 Hexanes:$CH_2Cl_2$ and the product was eluted with 5% MeOH in $CH_2Cl_2$. The solvent was removed in vacuo to afford 0.300 g (97%) as a white solid. MS (ES+) m/z 500.1 $(N+H)^+$.

EXAMPLE 1

{3-[3-(1-Amino-ethylidene)-5-chloro-2,4-dioxo-3,4-dihydro-2H-quinolin-1-yl]-cyclohexylmethyl}-carbamic Acid Benzyl Ester The compound of preparation 7 (0.4 g, 0.8 mmol) and $Mo(CO)_6$ (0.44 g, 1.7 mmol) were combined in a solution of acetonitrile (25 mL) and water (5 mL). The reaction mixture was heated to reflux while stirring. After stirring for 3 hr the reaction was complete. The reaction was concentrated to a dark brown solid under vacuum. The solid was diluted in $CH_2Cl_2$ (10 mL) and was purified by silica gel column chromatography using 50% EtOAc in CH2Cl2 to elute the product. The solvent was removed in vacuo to afford 0.325 g of desired product as a light yellow oil. MS (ES+) m/z 481.9 (M+H)$^+$, (ES−) 479.9 (M−H)$^−$.

EXAMPLE 2

N-{3-[3-(1-Amino-ethylidene)-5-chloro-2,4-dioxo-3, 4-dihydro-2H-quinolin-1-yl]-cyclohexylmethyl}-nicotinamide The compound of preparation 9 (0.02 g, 0.04 mmol) and Mo(CO)$_6$ (0.13 g, 0.5 mmol) were combined in a solution of acetonitrile (5 mL) and water (1 mL). The reaction mixture was heated to 60° C. and stirred for 2 hr. The reaction was concentrated to a dark brown solid under vacuum. The solid was diluted in CH2Cl$_2$ (10 mL) and purified by passing directly through a Bond-Elut cation exchange column. The product was eluted with 2M Ammonia in MeOH. The brown liquid was filtered using a Gelman Nylon Acrodisc to afford a yellow solution. The solvent was removed in vacuo to afford 0.018 g (90%) of a white solid. MS (ES+) m/z 452.9 (M+H)$^+$, (ES−) m/z 450.8 (M−H)$^−$, 510.9 (M+CH$_3$COO$^−$)$^−$.

EXAMPLE 3

N-{3-[3-(1-Amino-ethylidene)-5-chloro-2,44-dioxo-3,4-dihydro-2H-quinolin-1-yl]-cyclohexylmethyl}-6-fluoro-nicotinamide A compound from preparation 10 (0.05 g, 0.11 mmol) and Mo(CO)$_6$ (0.31 g, 1.2 mmol) were combined in a solution of acetonitrile (15 mL) and water (3 mL). The reaction mixture was heated to 60° C. and stirred for 2 hr. The reaction was concentrated to a dark brown solid under vacuum. The solid was diluted in CH$_2$Cl$_2$ (10 mL) and purified by silica gel column chromatography using 50% EtOAc in CH$_2$Cl$_2$ to elute the desired product. The solvent was removed in vacuo to afford 0.022 g (44%) of a white solid. MS (ES+) m/z 470.9 (M+H)$^+$, (ES−) m/z 468.8 (M−H)$^−$.

EXAMPLE 4

N-{3-[3-(1-Amino-ethylidene)-5-chloro-2,4-dioxo-3, 4-dihydro-2H-quinolin-1-yl]-cyclohexyimethyl}-benzamide The compound of preparation 11 (0.05 g, 0.1 mmol) and Mo(CO)$_6$ (0.3 g, 1.1 mmol) were combined in a solution of acetonitrile (5 mL) and water (1 mL)*. The reaction mixture was heated to 60° C. while stirring. After 3 hr of stirring the reaction was complete. The reaction was concentrated to a dark brown solid under vacuum. The solid was diluted in CH$_2$Cl$_2$ (1 mL) and purified by passing through a Varian Bond Elut SI column (5 g). The product was eluted with 2% MeOH in CH$_2$Cl$_2$. The solvent was removed in vacuo to afford 0.041 g of the title compound as a light brown solid, which was used as is in following experiments. MS (ES+) m/z 452.0 (M+H)$^+$, (ES−) 450.0 (M−H)$^−$.
*Skacani, I.; Fisera, L.; Bartovicova, M.; Varkonda, S.; Hyblova, O.; Collect Czech Chem Commun. 1991, 56 (9), 1926–1936.

The compounds of the invention are inhibitors of MRP1. Thus, the compounds of the invention may be used to inhibit any neoplasm having intrinsic and/or acquired resistance, conferred in part or in total by MRP1, to an oncolytic or oncolytics. In other words, treatment of such a neoplasm with an effective amount of a compound of this invention will cause the neoplasm to be more sensitive to chemotherapy that was rendered less efficacious by MR1.

Vincristine, epirubicin, daunorubicin, doxorubicin, and etoposide are oncolytics that are substrates of MRP1. See Cole, et. al., "Pharmacological Characterization of Multidrug Resistant MRP-transfected Human Tumor Cells", *Cancer Research*, 54:5902–5910, 1994. Since MR1 is ubiquitous in mammals, particularly humans, Nooter, K, et. al., "Expression of the Multidrug Resistance-Associated Protein (MRP) Gene in Human Cancers", *Clin. Can. Res.*, 1:1301–1310, (1995), chemotherapy whose goal is to inhibit a neoplasm employing any of those agents has the potential to be rendered less efficacious by MRP1. Thus, neoplasms of the bladder, bone, breast, lung(small-cell), testis, and thyroid and more specific types of cancer such as acute lymphoblastic and myeloblastic leukemia, Wilm's tumor, neuroblastoma, soft tissue sarcoma, Hodgkin's and non-Hodgkin's lymphomas, and bronchogenic carcinoma may be inhibited with a combination of one or more of the above oncolytics and a compound of this invention.

The biological activity of the compounds of the present invention was evaluated employing an initial screening assay, which rapidly and accurately measured the activity of the tested compound in inhibiting MRP1 or MDR1. Assays useful for evaluating this reversing capability are well known in the art. See, e.g., T. McGrath, et al., *Biochemical Pharmacology*, 38:3611, 1989; D. Marquardt and M. S. Center, *Cancer Research*, 52:3157, 1992; D. Marquardt, et al., *Cancer Research*, 50:1426, 1990; and Cole, et. al., *Cancer Research*, 54: 5902–5910, 1994.

Assay for Reversal of MRP1-Mediated Doxorubicin Resistance and MDR1-Mediated Vincristine Resistance: HL60/Adr and HL60/Vinc are continuous cell lines, which were selected for doxorubicin and vincristine resistance respectively by culturing HL60, a human acute myeloblastic leukemia cell line, in increasing concentrations of doxorubicin or vincristine until a highly resistant variant was attained.

HL60/Adr and HL60/Vinc cells were grown in RPMI 1640 (Gibco) containing 10% fetal bovine serum (FBS) and 50 μg/ml GENTAMICIN™ (Sigma). Cells were harvested; washed twice with assay medium (same as culture media); counted; and diluted to 1×10$^5$ cells/ml in assay medium. One hundred microliters of cells were aliquoted into wells of a 96 well tissue culture plate. Two columns of each 96 well plate served as a negative control and received assay medium containing no cells.

Test compounds and reference compounds were dissolved in dimethyl sulfoxide (DMSO) at a concentration of 5 mM. Samples were diluted in assay medium and 25 μl of each test compound was added to 8 wells. Assay standards were run in quadruplicate. Assay media was added to half of the wells and doxorubicin to the other half of the wells to achieve a final volume of 150 μl per well.

The plates were incubated at 37° C. for 72 hours in a humidified incubator with a 5% carbon dioxide atmosphere. Cell viability and vitality was measured by oxidation of a alamarBlue™ fluorescent dye using standard conditions. The plates were incubated for 3 hours at 37° C. Fluorescence was determined using 550 nm excitation and 590 nm emission using a microtitre plate reader.

The ability of a test compound to reverse the resistance of HL60/Adr and HL60/Vinc cells to doxorubicin was determined by comparison of the absorbance of the wells containing a test compound in addition to the oncolytic (doxorubicin) with the absorbance of wells containing the oncolytic without a test compound. Controls were used to eliminate background and to ensure the results were not artifactual. The results of the assay are expressed as percent inhibition of cell growth. The oncolytic alone at the tested concentration minimally inhibits the growth of HL60/Adr or HL60/Vinc cells.

Representative compounds of formula I demonstrated a significant effect in reversing the MRP1 multiple drug resistance. Many of the compounds showed very significant enhancement of activity in combination with the oncolytic agent as opposed to the oncolytic agent alone. In addition, a large majority of the compounds tested displayed a significant degree of selective inhibition of the HL60/Adr cell line over the HL60/Vinc cell line.

When administering an oncolytic in practicing the methods of this invention, the amount of oncolytic employed will be variable. It should be understood that the amount of the oncolytic actually administered will be determined by a physician, in the light of the relevant circumstances, including the condition to be treated, the chosen route of administration, the actual oncolytic administered, the age, weight, and response of the individual patient (mammal), and the severity of the patient's symptoms. Of course, the amount of oncolytic administered should be decided and closely monitored by that patient's physician. After deciding on the oncolytic or oncolytics to employ, "The Physician's Desk Reference®", published by Medical Economics Company at Montvale, N.J. 07645-1742, is a helpful resource to the physician in deciding on amounts of the oncolytic to administer and is updated annually.

Preferred formulations, and the methods of this invention employing those formulations, are those which do not contain an oncolytic. Thus, it is preferred to administer the compounds of this invention separately from the oncolytic. The oncolytics mentioned in this specification are commercially available and may be purchased in pre-formulated forms suitable for the methods of this invention.

The compounds of formula I alone, or optionally in combination with an oncolytic, are usually administered in the form of pharmaceutical formulations. These formulations can be administered by a variety of routes including oral, rectal, transdermal, subcutaneous, intravenous, intramuscular, and intranasal. Such formulations are prepared in a manner well known in the pharmaceutical art and comprise at least one active compound of formula I.

The present invention also includes methods employing pharmaceutical formulations, which contain, as the active ingredient, the compounds of formula I, and optionally an oncolytic, associated with pharmaceutical carriers. In making the formulations of the present invention the active ingredient(s) is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound(s) to provide the appropriate particle size prior to combining with the other ingredients. If the active compound(s) is substantially insoluble, it ordinarily is milled to a particle size of less than 200 mesh. If the active compound(s) is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystaline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The formulations of the invention can be formulated so as to provide quick, sustained or delayed release of the active ingredient after administration to the patient by employing procedures known in the art.

The formulations are preferably formulated in a unit dosage form, each dosage containing from about 5 to about 100 mg, more usually about 10 to about 30 mg, of each active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds of formula I are effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid formulations such as tablets the principal active ingredient(s) is mixed with a pharmaceutical excipient to form a solid preformulation composition containing a homogeneous mixture of a compound of the present invention. When referring to these preformulation compositions as homogeneous, it is meant that the active ingredient(s) is dispersed evenly throughout the formulation so that the formulation may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The novel formulations which are liquid forms may be incorporated for administration orally or by injection and include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Formulations for inhalation or insufflation include solutions and suspensions in pharmaceutical, aqueous or organic solvents, or mixtures thereof, and powders. The liquid or solid formulations may contain suitable pharmaceutical excipients as described supra. Preferably the formulations are administered by the oral or nasal respiratory route for local or systemic effect. Compositions in preferably pharmaceutical solvents may be nebulized by use of inert gases. Nebulized solutions may be breathed directly from the nebulizing device or the nebulizing device may be attached to a face mask, tent, or intermittent positive pressure breathing machine. Solution, suspension, or powder formulations may be administered, preferably orally or nasally, from devices, which deliver the formulation in an appropriate manner.

We claim:

1. A method of inhibiting MRP1 in a mammal which comprises administering to a mammal in need thereof an effective amount of a compound of formula I:

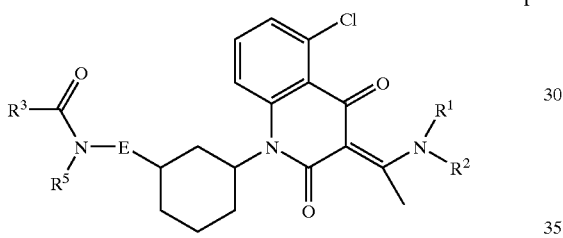

wherein:

E is a bond or —C($R^4$)($R^4$)—;

$R^1$ is independently at each occurrence hydrogen or $C_1$–$C_6$ alkyl;

$R^2$ is independently at each occurrence hydrogen or $C_1$–$C_6$ alkyl;

$R^3$ is independently at each occurrence hydrogen, $C_1$–$C_6$ alkyl, optionally substituted $C_3$–$C_8$ cycloalkyl, optionally substituted ($C_1$–$C_4$ alkyl) $C_3$–$C_8$ cycloalkyl, optionally substituted ($C_1$–$C_4$ alkyl)-aryl, optionally substituted aryl, optionally substituted ($C_1$–$C_4$ alkyl)-heterocycle, optionally substituted heterocycle, $C_1$–$C_6$ alkoxy, optionally substituted O—($C_3$–$C_8$ cycloalkyl), optionally substituted ($C_1$–$C_4$ alkoxy) $C_3$–$C_8$ cycloalkyl, optionally substituted ($C_1$–$C_4$ alkoxy)-aryl, optionally substituted O-aryl, optionally substituted ($C_1$–$C_4$ alkoxy)-heterocycle, or optionally substituted O-heterocycle;

$R^4$ is independently at each occurrence hydrogen or $C_1$–$C_6$ alkyl;

$R^5$ is independently at each occurrence hydrogen or $C_1$–$C_6$ alkyl; or a pharmaceutical salt thereof wherein:

optionally substituted $C_3$–$C_8$ cycloalkyl refers to a $C_3$–$C_8$ cycloalkyl unsubstituted or substituted once with a phenyl, substituted phenyl, or $CO_2R^1$ group;

optionally substituted ($C_1$–$C_4$ alkyl)-($C_3$–$C_8$ cycloalkyl) refers to optionally substituted $C_3$–$C_8$ cycloalkyl linked through a $C_1$–$C_4$ alkyl, optionally substituted with halo or hydroxy;

optionally substituted $C_6$–$C_{10}$ bicycloalkyl refers to a $C_6$–$C_{10}$ bicycloalkyl unsubstituted or substituted once with a phenyl, substituted phenyl, or $CO_2R^1$ group;

optionally substituted aryl refers to a phenyl and naphthyl group respectively optionally substituted from 1 to 5 times independently with $C_1$–$C_6$ alkyl, $C_1$–$C_4$ alkoxy, halo, hydroxy, trifluoromethyl, $NR^4R^5$, $SO_2N(R^{13})_2$, NH—Pg, $C_1$–$C_6$ alkoxy, benzyloxy, $C(O)R^{13}$, $C_5$–$C_7$ cycloalkyl, trifluoromethoxy, $SR^1$, cyano, or nitro;

optionally substituted ($C_1$–$C_4$ alkyl)-aryl refers to optionally substituted aryl linked through a $C_1$–$C_4$ alkyl, optionally substituted with halo, trifluoromethyl, or hydroxy;

optionally substituted phenoxy refers to a phenoxy group optionally substituted from 1 to 3 times independently with $C_1$–$C_6$ alkyl, halo, hydroxy, trifluoromethyl, $NR^4R^6$, $SO_2N(R^{13})_2$, NH—Pg, $C_1$–$C_6$ alkoxy, benzyloxy, $C(O)R^{13}$, $C_5$–$C_7$ cycloalkyl, trifluoromethoxy, or nitro;

optionally substituted ($C_1$–$C_4$ alkyl)-phenoxy refers to optionally substituted phenoxy linked through a $C_1$–$C_4$ alkyl, optionally substituted with halo, trifluoromethyl, or hydroxy;

heterocycle is taken to mean stable unsaturated and saturated 3 to 6 membered rings containing from 1 to 4 heteroatoms selected from the group consisting of nitrogen, oxygen and sulfur, said rings being optionally benzofused. All of these rings may be substituted with up to three substituents independently selected from the group consisting of halo, $C_1$–$C_4$ alkoxy, $C_1$–$C_4$ alkyl, cyano, nitro, hydroxy, —S(O)$_m$—($C_1$–$C_4$ alkyl) and —S(O)$_m$-phenyl where m is 0, 1 or 2;

heteroaryl is taken to mean an unsaturated or benzofused unsaturated heterocycle;

substituted heterocycle refers to a heterocyclic ring substituted 1 or 3 times independently with a $C_1$–$C_6$ alkyl, halo, benzyl, phenyl, trifluoromethyl. Saturated heterocyclic rings may be additionally substituted 1 or 2 times with an oxo group, however, total substitution of the saturated heterocyclic ring may not exceed two substituents; and optionally substituted ($C_1$–$C_4$ alkyl)-heterocycle refers to optionally substituted heterocycle linked through a $C_1$–$C_4$ alkyl, optionally substituted with halo or hydroxy.

2. A method of inhibiting a resistant neoplasm, or a neoplasm susceptible to resistance in a mammal wherein the resistance is conferred in part, or in total, by MRP1 which comprises administering to a mammal in need thereof an effective amount of a compound of formula I:

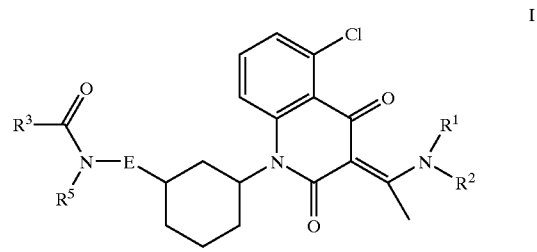

wherein:

23

E is a bond or —C(R⁴)(R⁴)—;
R¹ is independently at each occurrence hydrogen or $C_1$–$C_6$ alkyl;
R² is independently at each occurrence hydrogen or $C_1$–$C_6$ alkyl;
R³ is independently at each occurrence hydrogen, $C_1$–$C_6$ alkyl, optionally substituted $C_3$–$C_8$ cycloalkyl, optionally substituted ($C_1$–$C_4$ alkyl $C_3$–$C_8$ cycloalkyl, optionally substituted ($C_1$–$C_4$ alkyl)-aryl, optionally substituted aryl, optionally substituted ($C_1$–$C_4$ alkyl)-heterocycle, optionally substituted heterocycle, $C_1$–$C_6$ alkoxy, optionally substituted O—($C_3$–$C_8$ cycloalkyl), optionally substituted ($C_1$–$C_4$ alkoxy) $C_3$–$C_8$ cycloalkyl, optionally substituted ($C_1$–$C_4$ alkoxy)-aryl, optionally substituted O-aryl, optionally substituted ($C_1$–$C_4$ alkoxy)-heterocycle, or optionally substituted O-heterocycle;
R⁴ is independently at each occurrence hydrogen or $C_1$–$C_6$ alkyl;
R⁵ is independently at each occurrence hydrogen or $C_1$–$C_6$ alkyl; or a pharmaceutical salt thereof
wherein:
optionally substituted $C_3$–$C_8$ cycloalkyl refers to a $C_3$–$C_8$ cycloalkyl unsubstituted or substituted once with a phenyl, substituted phenyl, or $CO_2R^1$ group;
optionally substituted ($C_1$–$C_4$ alkyl)-($C_3$–$C_8$ cycloalkyl) refers to optionally substituted $C_3$–$C_8$ cycloalkyl linked through a $C_1$–$C_4$ alkyl, optionally substituted with halo or hydroxy;
optionally substituted $C_6$–$C_{10}$ bicycloalkyl refers to a $C_6$–$C_{10}$ bicycloalkyl unsubstituted or substituted once with a phenyl, substituted phenyl, or $CO_2R^1$ group;
optionally substituted aryl refers to a phenyl and naphthyl group respectively optionally substituted from 1 to 5 times independently with $C_1$–$C_6$ alkyl, $C_1$–$C_4$ alkoxy, halo, hydroxy, trifluoromethyl, $NR^4R^5$, $SO_2N(R^{13})_2$, NH—Pg, $C_1$–$C_6$ alkoxy, benzyloxy, $C(O)R^{13}$, $C_5$–$C_7$ cycloalkyl, trifluoromethoxy, $SR^1$, cyano, or nitro;
optionally substituted ($C_1$–$C_4$ alkyl)-aryl refers to optionally substituted aryl linked through a $C_1$–$C_4$ alkyl, optionally substituted with halo, trifluoromethyl, or hydroxy;
optionally substituted phenoxy refers to a phenoxy group optionally substituted from 1 to 3 times independently with $C_1$–$C_6$ alkyl, halo, hydroxy, trifluoromethyl, $NR^4R^6$, $SO_2N(R^{13})_2$, NH—Pg, $C_1$–$C_6$ alkoxy, benzyloxy, $C(O)R^{13}$, $C_5$–$C_7$ cycloalkyl, trifluoromethoxy, or nitro;
optionally substituted ($C_1$–$C_4$ alkyl)-phenoxy refers to optionally substituted phenoxy linked through a $C_1$–$C_4$ alkyl, optionally substituted with halo, trifluoromethyl, or hydroxy;
heterocycle is taken to mean stable unsaturated and saturated 3 to 6 membered rings containing from 1 to 4 heteroatoms selected from the group consisting of nitrogen, oxygen and sulfur, said rings being optionally benzofused. All of these rings may be substituted with up to three substituents independently selected from the group consisting of halo, $C_1$–$C_4$ alkoxy, $C_1$–$C_4$ alkyl, cyano, nitro, hydroxy, —S(O)$_m$—($C_1$–$C_4$ alkyl) and —S(O)$_m$-phenyl where m is 0, 1 or 2;
heteroaryl is taken to mean an unsaturated or benzofused unsaturated heterocycle;

24 substituted heterocycle refers to a heterocyclic ring substituted 1 or 3 times independently with a $C_1$–$C_6$ alkyl, halo, benzyl, phenyl, trifluoromethyl. Saturated heterocyclic rings may be additionally substituted 1 or 2 times with an oxo group, however, total substitution of the saturated heterocyclic ring may not exceed two substituents; and
optionally substituted ($C_1$–$C_4$ alkyl)-heterocycle refers to optionally substituted heterocycle linked through a $C_1$–$C_4$ alkyl, optionally substituted with halo or hydroxy;
in combination with an effective amount of an oncolytic agent.

3. A pharmaceutical formulation comprising a compound of formula I:

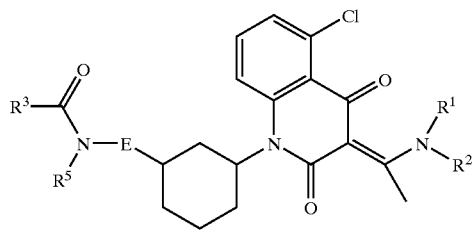

wherein:
E is a bond or —C(R⁴)(R⁴)—;
R¹ is independently at each occurrence hydrogen or $C_1$–$C_4$ alkyl;
R² is independently at each occurrence hydrogen or $C_1$–$C_6$ alkyl;
R³ is independently at each occurrence hydrogen, $C_1$–$C_6$ alkyl, optionally substituted $C_3$–$C_8$ cycloalkyl, optionally substituted ($C_1$–$C_4$ alkyl) $C_3$–$C_8$ cycloalkyl, optionally substituted ($C_1$–$C_4$ alkyl)-aryl, optionally substituted aryl, optionally substituted ($C_1$–$C_4$ alkyl)-heterocycle, optionally substituted heterocycle, $C_1$–$C_6$ alkoxy, optionally substituted O—($C_3$–$C_8$ cycloalkyl), optionally substituted ($C_1$–$C_4$ alkoxy) $C_3$–$C_8$ cycloalkyl, optionally substituted ($C_1$–$C_4$ alkoxy)-aryl, optionally substituted O-aryl, optionally substituted ($C_1$–$C_4$ alkoxy)-heterocycle, or optionally substituted O-heterocycle;
R⁴ is independently at each occurrence hydrogen or $C_1$–$C_6$ alkyl;
R⁵ is independently at each occurrence hydrogen or $C_1$–$C_6$ alkyl; or a pharmaceutical salt thereof
wherein:
optionally substituted $C_3$–$C_8$ cycloalkyl refers to a $C_3$–$C_8$ cycloalkyl unsubstituted or substituted once with a phenyl, substituted phenyl, or $CO_2R^1$ group;
optionally substituted ($C_1$–$C_4$ alkyl)-($C_3$–$C_8$ cycloalkyl) refers to optionally substituted $C_3$–$C_8$ cycloalkyl linked through a $C_1$–$C_4$ alkyl, optionally substituted with halo or hydroxy;
optionally substituted $C_6$–$C_{10}$ bicycloalkyl refers to a $C_6$–$C_{10}$ bicycloalkyl unsubstituted or substituted once with a phenyl, substituted phenyl, or $CO_2R^1$ group;
optionally substituted aryl refers to a phenyl and naphthyl group respectively optionally substituted from 1 to 5 times independently with $C_1$–$C_6$ alkyl, $C_1$–$C_4$ alkoxy, halo, hydroxy, trifluoromethyl, $NR^4R^5$, $SO_2N(R^{13})_2$, MH—Pg, $C_1$–$C_6$ alkoxy, benzyloxy, C(O)R$^{13}$, C$_5$–C$_7$ cycloalkyl, trifluoromethoxy, SR$^1$, cyano, or nitro;

optionally substituted (C$_1$–C$_4$ alkyl)-aryl refers to optionally substituted aryl linked through a C$_1$–C$_4$ alkyl, optionally substituted with halo, trifluoromethyl, or hydroxy;

optionally substituted phenoxy refers to a phenoxy group optionally substituted from 1 to 3 times independently with C$_1$–C$_6$ alkyl, halo, hydroxy, trifluoromethyl, NR$^4$R$^6$, SO$_2$N(R$^{13}$)$_2$, MH—Pg, C$_1$–C$_6$ alkoxy, benzyloxy, C(O)R$^{13}$, C$_5$–C$_7$ cycloalkyl, trifluoromethoxy, or nitro;

optionally substituted (C$_1$–C$_4$ alkyl)-phenoxy refers to optionally substituted phenoxy linked through a C$_1$–C$_4$ alkyl, optionally substituted with halo, trifluoromethyl, or hydroxy;

heterocycle is taken to mean stable unsaturated and saturated 3 to 6 membered rings containing from 1 to 4 heteroatoms selected from the group consisting of nitrogen, oxygen and sulfur, said rings being optionally benzofused. All of these rings may be substituted with up to three substituents independently selected from the group consisting of halo, C$_1$–C$_4$ alkoxy, C$_1$–C$_4$ alkyl, cyano, nitro, hydroxy, —S(O)$_m$—(C$_1$–C$_4$ alkyl) and —S(O)$_m$-phenyl where m is 0, 1 or 2;

heteroaryl is taken to mean an unsaturated or benzofused unsaturated heterocycle;

substituted heterocycle refers to a heterocyclic ring substituted 1 or 3 times independently with a C$_1$–C$_6$ alkyl, halo, benzyl, phenyl, trifluoromethyl. Saturated heterocyclic rings may be additionally substituted 1 or 2 times with an oxo group, however, total substitution of the saturated heterocyclic ring may not exceed two substituents; and optionally substituted (C$_1$–C$_4$ alkyl)-heterocycle refers to optionally substituted heterocycle linked through a C$_1$–C$_4$ alkyl, optionally substituted with halo or hydroxy;

in combination with one or more oncolytics, pharmaceutical carriers, diluents, or excipients therefor.

4. A pharmaceutical formulation comprising a compound of formula I:

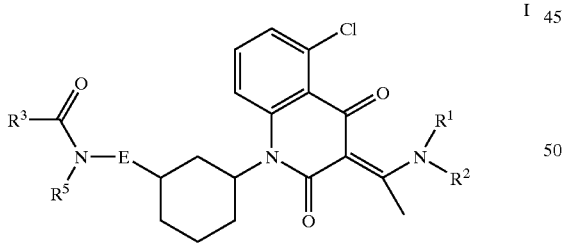

I wherein:

E is a bond or —C(R$^4$)(R$^4$)—;

R$^1$ is independently at each occurrence hydrogen or C$_1$–C$_6$ alkyl;

R$^2$ is independently at each occurrence hydrogen or C$_1$–C$_6$ alkyl;

R$^3$ is independently at each occurrence hydrogen, C$_1$–C$_6$ alkyl, optionally substituted C$_3$–C$_8$ cycloalkyl, optionally substituted (C$_1$–C$_4$ alkyl) C$_3$–C$_8$ cycloalkyl, optionally substituted (C$_1$–C$_4$ alkyl)-aryl, optionally substituted aryl, optionally substituted (C$_1$–C$_4$ alkyl)-heterocycle, optionally substituted heterocycle, C$_1$–C$_6$ alkoxy, optionally substituted O—(C$_3$–C$_8$ cycloalkyl), optionally substituted (C$_1$–C$_4$ alkoxy) C$_3$–C$_8$ cycloalkyl, optionally substituted (C$_1$–C$_4$ alkoxy)-aryl, optionally substituted O-aryl, optionally substituted (C$_1$–C$_4$ alkoxy)-heterocycle, or optionally substituted O-heterocycle;

R$^4$ is independently at each occurrence hydrogen or C$_1$–C$_6$ alkyl;

R$^5$ is independently at each occurrence hydrogen or C$_1$–C$_6$ alkyl; or a pharmaceutical salt thereof wherein:

optionally substituted C$_3$–C$_8$ cycloalkyl refers to a C$_3$–C$_8$ cycloalkyl unsubstituted or substituted once with a phenyl, substituted phenyl, or CO$_2$R$^1$ group;

optionally substituted (C$_1$–C$_4$ alkyl)-(C$_3$–C$_8$ cycloalkyl) refers to optionally substituted C$_3$–C$_8$ cycloalkyl linked through a C$_1$–C$_4$ alkyl, optionally substituted with halo or hydroxy;

optionally substituted C$_6$–C$_{10}$ bicycloalkyl refers to a C$_6$–C$_{10}$ bicycloalkyl unsubstituted or substituted once with a phenyl, substituted phenyl, or CO$_2$R$^1$ group;

optionally substituted aryl refers to a phenyl and naphthyl group respectively optionally substituted from 1 to 5 times independently with C$_1$–C$_6$ alkyl, C$_1$–C$_4$ alkoxy, halo, hydroxy, trifluoromethyl, NR$^4$R$^5$, SO$_2$N(R$^{13}$)$_2$, NH—Pg, C$_1$–C$_6$ alkoxy, benzyloxy, C(O)R$^{13}$, C$_5$–C$_7$ cycloalkyl, trifluoromethoxy, SR$^1$, cyano, or nitro;

optionally substituted (C$_1$–C$_4$ alkyl)-aryl refers to optionally substituted aryl linked through a C$_1$–C$_4$ alkyl, optionally substituted with halo, trifluoromethyl, or hydroxy;

optionally substituted phenoxy refers to a phenoxy group optionally substituted from 1 to 3 times independently with C$_1$–C$_6$ alkyl, halo, hydroxy, trifluoromethyl, NR$^4$R$^6$, SO$_2$N(R$^{13}$)$_2$, MH—Pg, C$_1$–C$_6$ alkoxy, benzyloxy, C(O)R$^{13}$, C$_5$–C$_7$ cycloalkyl, trifluoromethoxy, or nitro;

optionally substituted (C$_1$–C$_4$ alkyl)-phenoxy refers to optionally substituted phenoxy linked through a C$_1$–C$_4$ alkyl, optionally substituted with halo, trifluoromethyl, or hydroxy;

heterocycle is taken to mean stable unsaturated and saturated 3 to 6 membered rings containing from 1 to 4 heteroatoms selected from the group consisting of nitrogen, oxygen and sulfur, said rings being optionally benzofused. All of these rings may be substituted with up to three substituents independently selected from the group consisting of halo, C$_1$–C$_4$ alkoxy, C$_1$–C$_4$ alkyl, cyano, nitro, hydroxy, —S(O)$_m$—(C$_1$–C$_4$ alkyl) and —S(O)$_m$-phenyl where m is 0, 1 or 2;

heteroaryl is taken to mean an unsaturated or benzofused unsaturated heterocycle;

substituted heterocycle refers to a heterocyclic ring substituted 1 or 3 times independently with a C$_1$–C$_6$ alkyl, halo, benzyl, phenyl, trifluoromethyl. Saturated heterocyclic rings may be additionally substituted 1 or 2 times with an oxo group, however, total substitution of the saturated heterocyclic ring may not exceed two substituents; and optionally substituted (C$_1$–C$_4$ alkyl)-heterocycle refers to optionally substituted heterocycle linked through a C$_1$–C$_4$ alkyl, optionally substituted with halo or hydroxy.

* * * * *